(12) United States Patent
Jeon et al.

(10) Patent No.: US 10,045,993 B2
(45) Date of Patent: Aug. 14, 2018

(54) PHARMACEUTICAL PREPARATION CONTAINING ENTECAVIR AS ACTIVE INGREDIENT, AND PREPARATION METHOD THEREFOR

(71) Applicant: CTC BIO, INC., Seoul (KR)

(72) Inventors: Hong Ryeol Jeon, Gyeonggi-do (KR); Do-Woo Kwon, Chungcheongnam-do (KR); Bong-Sang Lee, Gyeonggi-do (KR); Su-Jun Park, Gyeonggi-do (KR); Jiyeong Han, Ulsan (KR); Myeongcheol Kil, Jeollabuk-do (KR); Min Seop Kim, Seoul (KR)

(73) Assignee: CTC BIO, INC., Seoul (KR)

( * ) Notice: Subject to any disclaimer, the term of this patent is extended or adjusted under 35 U.S.C. 154(b) by 0 days.

(21) Appl. No.: 15/320,446

(22) PCT Filed: Jun. 22, 2015

(86) PCT No.: PCT/KR2015/006329
§ 371 (c)(1),
(2) Date: Dec. 20, 2016

(87) PCT Pub. No.: WO2015/194923
PCT Pub. Date: Dec. 23, 2015

(65) Prior Publication Data
US 2017/0136025 A1 May 18, 2017

(30) Foreign Application Priority Data
Jun. 20, 2014 (KR) .................. 10-2014-0075457

(51) Int. Cl.
*A61K 31/522* (2006.01)
*A61K 9/00* (2006.01)
*A61K 47/10* (2017.01)

(52) U.S. Cl.
CPC ............ *A61K 31/522* (2013.01); *A61K 9/006* (2013.01); *A61K 47/10* (2013.01)

(58) Field of Classification Search
CPC ...... A61K 31/522; A61K 47/10; A61K 9/006; A61K 31/05; A61K 31/215; A61K 47/06
See application file for complete search history.

(56) References Cited

U.S. PATENT DOCUMENTS

2001/0033864 A1* 10/2001 Colonno .............. A61K 9/2018
424/451
2011/0290694 A1* 12/2011 Fuisz ........................ A61J 3/00
206/459.5
2012/0328675 A1    12/2012 Awamura et al. ............ 424/400

FOREIGN PATENT DOCUMENTS

| CN | 101278938 | | 10/2008 | |
| CN | 101756890 | A | 6/2010 | |
| CN | 103181903 | A | 7/2013 | |
| CN | 103301071 | A | 9/2013 | |
| KR | 10-2013-0029758 | | 3/2013 | |
| KR | 20140120275 | A | 10/2014 | |
| WO | WO 2013/072937 | | 5/2013 | |
| WO | WO 2013/114389 | | 8/2013 | |
| WO | WO 2013/177672 | | 12/2013 | |
| WO | WO-2013177672 A1 * | | 12/2013 | ............. A61K 38/21 |

OTHER PUBLICATIONS

Ramesh et al, J Sep Sci Feb. 2014;37(4):368-75.*
Puz et al, Journal Pharmaceutical Development and Technology vol. 10, 2005—Issue 1.*
International Search Report (ISR) dated Sep. 25, 2015 in PCT/KR2015/006329 published as WO 2015/194923.

* cited by examiner

*Primary Examiner* — Jean P Cornet
(74) *Attorney, Agent, or Firm* — Harness, Dickey & Pierce, P.L.C.

(57) ABSTRACT

The present invention relates to a pharmaceutical preparation comprising entecavir as an active ingredient, wherein an antioxidizing agent is added to enhance stability of entecavir, and a method for preparing the same. According to the present invention, the invention has an effect that entecavir can be stably maintained in a pharmaceutical preparation containing a certain amount or more of moisture by adding the antioxidizing agent, thereby a pharmaceutical preparation can be provided as a formulation containing a certain amount or more of moisture, for example, an orally disintegrating film formulation.

6 Claims, No Drawings

PHARMACEUTICAL PREPARATION CONTAINING ENTECAVIR AS ACTIVE INGREDIENT, AND PREPARATION METHOD THEREFOR

CROSS-REFERENCE TO RELATED APPLICATIONS

This application is a national phase application of PCT Application No. PCT/KR2015/006329, filed on 22 Jun. 2015, which claims benefit of Korean Patent Application No. KR 10-2014-0075457 filed 20 Jun. 2014. The entire disclosures of the applications identified in this paragraph are incorporated herein by references.

FIELD

The present disclosure relates to a pharmaceutical preparation comprising entecavir as an active ingredient and a method for preparing the same, and more specifically, it relates to a method for stably maintaining entecavir in a pharmaceutical preparation containing moisture without being hydrolyzed.

BACKGROUND

Entecavir, [1-S-(1α,3α,4β)]-2-amino-1,9-dihydro-9-[4-hydroxy-3-(hydroxymethyl)-2-methylenecyclopentyl]-6H-purin-6-one, is an antiviral agent being used for treating hepatitis B virus infection, whose three dimensional structure is composed of a cyclopentane having purine at 1S-position, exomethylene at 2-position, hydroxymethyl at 3R-position, and hydroxy at 4S-position. Entecavir is activated as entecavir triphosphate form by phosphorylation, and exhibits a treatment effect for hepatitis B. Commercially available therapeutic agents for hepatitis B contain 0.5 mg or 1 mg entecavir anhydride per unit dose.

Entecavir has moisture solubility of 2.4 mg/ml at pH 7.9, 25° C. (room temperature), and shows low stability to moisture because it is hydrolyzed in the presence of moisture. Hydrolysis of entecavir leads to reduction of therapeutic effect, and therefore, it is necessary to secure moisture-stability of entecavir.

In the case of a drug showing low moisture-stability, for blocking contact with moisture commonly present outside of a preparation, methods such as moisture-proof coating or sealing for preservation and the like are used, and methods such as minimizing moisture content in a preparation or replacing with other materials (for example, glycerin, propylene glycol, alcohol and the like) and the like are also used.

However, in the case of a pharmaceutical preparation which should contains a certain content or more of moisture in a preparation, as a pharmaceutical preparation containing entecavir, a method for enhancing stability to moisture contained in the preparation in addition to block moisture outside of the preparation.

DISCLOSURE

Technical Problem

The present disclosure is designed to solve the problems of the related art, and therefore the present disclosure is directed to providing a method for stably maintaining entecavir in a pharmaceutical preparation containing a certain content or more of moisture and a pharmaceutical preparation prepared by the method.

Further, the present disclosure is directed to providing a pharmaceutical preparation comprising entecavir as an active ingredient as an orally disintegrating (dissolving) formulation, which can be immediately dissolved (or disintegrated) when orally administered, and therefore, a drug can be absorbed.

These and other objects and advantages of the present disclosure may be understood from the following detailed description and will become more fully apparent from the exemplary embodiments of the present disclosure. Also, it will be easily understood that the objects and advantages of the present disclosure may be realized by the means shown in the appended claims and combinations thereof.

Technical Solution

In one aspect of the present disclosure, the present invention relates to a pharmaceutical preparation comprising entecavir as an active ingredient, which comprises at least one antioxidizing agent for enhancing moisture-stability of entecavir, and has LOD (%) of 1% or more but less than 10%, which is measured at 105° C. for 4 hours in accordance with USP 731.

Further, the present invention relates to a use of at least one antioxidizing agent for enhancing moisture-stability of entecavir in the pharmaceutical preparation comprising entecavir as an active ingredient and having LOD (%) of 1% or more but less than 10%, which is measured at 105° C. for 4 hours in accordance with USP 731.

The present inventors found that when adding an antioxidizing agent, characteristics of entecavir which is difficult to be stably maintained and is weak on moisture-stability because it is hydrolyzed by moisture in the pharmaceutical preparation comprising a certain content or more of moisture, can be overcome, and completed the present invention.

For example, in the case of a pharmaceutical preparation as an orally dissolving (disintegrating) formulation, its LOD (%) measured at 105° C. for 4 hours in accordance with USP 731 should be 1% or more, but it is difficult to formulate entecavir which is weak on moisture to an orally dissolving (disintegrating) formulation (e.g. orally disintegrating film). However, if the antioxidizing agent is added according to the present invention, there is an effect that entecavir can be stably maintained even in this preparation having excessive moisture content.

The pharmaceutical preparation according to the present invention can be any pharmaceutical preparation comprising entecavir as an active ingredient, and for example, it may include a pharmaceutical preparation for treating or preventing hepatitis B.

In the present invention, 'stability to moisture' or 'moisture-stability' means stability to water, and in particular, it means stability to water contained in a pharmaceutical preparation. It refers to a characteristic that physical and chemical characteristics of entecavir can be maintained in a pharmaceutical preparation without any change, and in particular, it includes a characteristic that entecavir can be maintained without be hydrolyzed after reacted with water.

In the present invention, 'entecavir' includes its pharmaceutically acceptable salt, and the 'pharmaceutically acceptable salt' refers to any organic or inorganic compound addition salt whose effective concentration has effective action because it is relatively non-toxic and harmless to the patients and whose side effects do not degrade the beneficial efficacy of entecavir. For example, free acid may be organic acid and inorganic acid or its non-toxic salts and the like, and the inorganic acid may be hydrochloric acid, phosphoric acid, sulfuric acid, nitric acid, tartaric acid and the like, and the organic acid may be methane sulfonic acid, p-toluene sulfonic acid, acetic acid, trifluoroacetic acid, maleic acid, succinic acid, oxalic acid, benzoic acid, tartaric acid, fumaric acid, manderic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid and the like. The acid addition salt may be prepared by a usual method, for example, dissolving a compound in the excessive quantity of aqueous acid solution followed by the precipitating the resulting salt using water-miscible organic solvent such as methanol, ethanol, acetone or acetonitrile. The compound of same molar amount and acid or alcohol in water can be heated and subsequently, the resulting mixture can be dried by evaporating, or precipitated salts can be filtered by suction. The non-toxic salts may be sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutylate, caprate, heptanoate, propiolate, oxalate, malonate, succinate, suberate, cebacate, fumarate, maliate, butyne-1,4-dioate, hexane-1,6-dioate, benzoate, chlorobenzoate, methylbenzoate, dinitrobenzoate, hydroxybenzoate, methoxybenzoate phthalate, terephthalate, benzenesulfonate, toluenesulfonate, chlorobenzenesulfonate, xylenesulfonate, phenylacetate, phenylpropionate, phenylbutylate, citrate, lactate, beta-hydroxybutylate, glycolate, malate, tartrate, methanesulfonate, propanesulfonate, naphthalene-1-sulfonate, naphthalene-2-sulfonate, or mandelate.

Therapeutically effective amount of entecavir can be included in the pharmaceutical preparation according to the present invention. For example, 0.5 mg to 1 mg of entecavir as a unit daily dosage can be subdividedly included.

In the present invention, the 'antioxidizing agent' has the same meaning with 'oxidation inhibitor', and it is a material blocking oxidation reaction. For example, it can be at least one selected from the group consisting of propyl gallate, dried sodium sulfite, butyl hydroxy toluene, sodium lauryl sulfate, retinol palmitate, riboflavin, sodium sulfate, zinc oxide, sorbic acid, magnesium stearate, sodium citrate hydrate, anhydrous citric acid, citric acid hydrate, diisopropyl adipate, ascorbic acid, sodium ascorbate, ascorbyl palmitate, sodium bisulfite, disodium edetate hydrate, oxy benzone, silicon dioxide, medium chain triglyceride, sodium bicarbonate, tocopherol, tocopherol acetate, benzophenone, butyl hydroxy anisole, butyl hydroxy toluene, sodium thiosulfate hydrate, sodium pyrosulfite, potassium pyrosulfite, D-mannitol, D-sorbitol and L-cysteine hydrochloride hydrate, and preferably it may be butyl hydroxy toluene, butyl hydroxy anisole, or a mixture of at least two thereof.

In the pharmaceutical preparation according to the present invention, weight ratio of entecavir:antioxidizing agent may be 1000:1 to 1:100, preferably 100:1 to 1:30, more preferably 50:1 to 1:10, 40:1 to 1:10, most preferably 30:1 to 1:10. If weight ratio of entecavir:antioxidizing agent is less than 1000:1, it may be difficult to secure moisture-stability of entecavir in a preparation containing large amount of moisture, and if weight ratio of entecavir:antioxidizing agent is more than 1:100, it may be difficult to prepare a pharmaceutical preparation as a formulation having a limit to the amount used. Further, it is not suitable for an orally disintegrating formulation because it takes longer time to be disintegrated in the mouth due to excessive amount of the antioxidizing agent used. If butyl hydroxy toluene, butyl hydroxy anisole or a mixture thereof as an antioxidizing agent is used, a enough moisture-stability effect can be exhibited even though the amount of the antioxidizing agent used is reduced to 1/30 or less of entecavir. Thus, it can be effective to a pharmaceutical preparation as an orally disintegrating formulation (e.g. film formulation).

Moisture content of the pharmaceutical preparation according to the present invention as LOD (%) measured at 105° C., for 4 hours in accordance with USP 731 may be 1% or more, 2% or more, 3% or more, 4% or more, 5% or more, 6% or more, 7% or more, less than 10%. Moisture content of a pharmaceutical preparation as LOD (%) measured at 105° C., for 4 hours in accordance with USP 731 may be 1% or more but 7% or less in the case of a solid preparation, or 2% or more but 10% or less in the case of a film preparation. The condition for measuring LOD (%), 105° C. and 4 hours, is the optimum condition for identifying the moisture content in a pharmaceutical preparation, and it may be conducted, for example, at 105° C. for 5 hours, but the disclosure of the present invention is not limited to the above condition.

The pharmaceutical preparation according to the present invention can further comprise a pharmaceutically acceptable carrier, which can be commonly added to a pharmaceutical preparation. The pharmaceutically acceptable carrier may include additives commonly used in the pharmacology field, such as excipients, disintegrating agents, binding agents, lubricants, emulsifiers, suspending agents, stabilizers, pH modifiers and the like, and as occasion demands, sweetening agents, flavors and/or pigments and the like can be additionally added. The excipients may include non-crystalline cellulose, starch, silicon dioxide (SiO2), sugar esters, Ludipress lactose, sucrose, maltose, fructose, sorbitol and the like. Preferably, a mixture of lactose and silicon dioxide may be used. The amount of the excipient used may be about 90 wt % or less based on the total weight of a pharmaceutical preparation, but not limited thereto. The disintegrating agent may include carboxymethylcellulose calcium (CMC-Ca), carboxymethylcellulose sodium (CMC-Na), cross povidone, alginic acid and the like. The amount of the disintegrating agent used may be in a rage of 3 to 16 wt % based on the total weight of a pharmaceutical preparation, but not limited thereto. The lubricant may include stearic acid, magnesium stearate, zinc stearate, glyceryl behenate, glyceryl palmitostearate, talc and the like, and it can be used in an amount of about 3 wt % or less based on the total weight of a pharmaceutical preparation, but not limited thereto.

Besides entecavir, as an active ingredient, other drugs can be added to the pharmaceutical preparation according to the present invention unless not hindering the object of the present invention, and for example, an additional anti-hepatitis B viral agent can be included.

The pharmaceutical preparation according to the present invention can be administered in combination with or alternatively with additional anti-hepatitis B viral agents, and the agent can be randomly selected from, for example, interferon alpha-2b, peginterferon alpha-2a, lamivudine, telbivudine, racivir, emtricitabine, clevudine, amdoxovir, valtorcitabine, tenofovir and adefovir. Besides the drugs mentioned above, a person skilled in the art can additionally select and use various drugs as occasion demands.

The pharmaceutical preparation according to the present invention can be formulated for oral administration, and for example, it can be formulated to various forms such as tablets, films, suspensions, granules, gels, pills, tinctures, decoctions, infusions, spirits, fluid extracts, elixirs, extracts, syrups, powders, aromatic moistures, lemonades and the like. Further, the tablets may be formulated to various forms such as orally disintegrating tablets, muco-adhesive tablets, dispersible tablets, sublingual tablets, buccal tablets, chewable tablets, dispensing tablets, multi-layered tablets, press-coated tablets, effervescent tablets (foaming tablets), solution tablets and the like. And a person skilled in the art can variously modify and use the various tables as occasion demands. More preferably, it may be a formulation disintegrated (dissolved) in the mouth (i.e., disintegrable in the mouth, dissolvable in the mouth), for example, a formulation dispersable (dissolvable) in the mouth, for example, orally dissolving film, orally disintegrating tablets, suspensions, suspension tablets, immediately disintegrating tablets, orally disintegrating granules, orally disintegrating troches, sublingual tablets, powders and/or chewable tablets, and considering various purposes, the formulation of the pharmaceutical preparation according to the present invention may preferably be an orally dissolving film formulation. The orally dissolving film may be interchangeably used with terms such as film, strip, orally disintegrating film and the like, and it refers to a formulation administered by attaching and dissolving the film in the mouth such as on top and below the tongue, oral mucosa and the like. The pharmaceutical preparation as an orally disintegrating film formulation according to the present invention has an advantage that it can be administered without water.

In other aspect, in the method for preparing the pharmaceutical preparation comprising entecavir as an active ingredient, the present invention provides a method for preparing a pharmaceutical preparation characterized by comprising steps of: adding at least one antioxidizing agent and entecavir; and drying the pharmaceutical preparation to have moisture content of 1% or more of LOD (%), wherein the LOD (%) is measured at 105° C. for 4 hours in accordance with USP 731.

According to the preparation method of the present invention, an orally disintegrating film having the final moisture content as LOD (%) measured at 105° C. for 4 hours in accordance with USP 731 of 1% or more can be provided by drying an orally disintegrating film solution wherein entecavir is stabilized in water solvent by adding an antioxidizing agent.

Advantageous Effects

The present disclosure gives the following effects.

According to the present invention, the invention has an excellent effect that entecavir can be stably maintained in a pharmaceutical preparation containing a certain amount or more of moisture by adding the antioxidizing agent, thereby a pharmaceutical preparation can be provided as a formulation containing a certain amount or more of moisture, for example, an orally disintegrating film formulation.

BEST MODE

Hereinafter, preferred embodiments of the present disclosure will be described in detail with reference to the accompanying drawings. Prior to the description, it should be understood that the terms used in the specification and the appended claims should not be construed as limited to general and dictionary meanings, but interpreted based on the meanings and concepts corresponding to technical aspects of the present disclosure on the basis of the principle that the inventor is allowed to define terms appropriately for the best explanation. Therefore, the description proposed herein is just a preferable example for the purpose of illustrations only, not intended to limit the scope of the disclosure, so it should be understood that other equivalents and modifications could be made thereto without departing from the scope of the disclosure.

MODE FOR DISCLOSURE

Example 1. Preparation of Orally Disintegrating Film Comprising Entecavir as Active Ingredient An entecavir containing orally disintegrating film whose stability to moisture is enhanced is prepared by the method described below.

Additives (ingredients and amounts thereof as described in the following Table 1 and Table 3) was added to water as a solvent, dissolved or dispersed therein by stirring, and then homogenized by using a homogenizer (Ultra turrax T-25, IKA). Entecavir was put and dissolved therein, and then a polymer (flurane, hydroxypropylcellulose, hydroxypropylmethylcellulose, povidone, polyvinylalcohol-polyethyleneglycol copolymer, or a mixture thereof) was added thereto. The resulting solution was homogenized again by using the same homogenizer, and then an antioxidizing agent (antioxidizing agent and amounts thereof as described in the following Table 1 and Table 3), which was separately dissolved in a proper solvent (ethanol, methanol, acetone, mineral oil, or a mixture thereof), was added thereto and homogenized. Then, gas was removed from the solution for preparing film under vacuum, and the solution was coated on a PET (polyethylene terephthalate) film, and then dried at 60 to 80° C. to obtain a film preparation comprising entecavir.

Test Example

Stability Test Method
In order to confirm assay (%) and total impurities (%), HPLC (Liquid chromatography) was conducted, and a test solution for HPLC was prepared by the following method.
Preparation of Test Solution
A film containing entecavir anhydride 1 mg was taken and put into a 10 ml flask, and mixed with mobile phase. The mixed solution was put into a centrifuge and centrifuged for 20 min. The centrifuged solution was filtered through a 0.2 μm filter (water soluble PTFE). As a result, a test solution (0.1 mg/ml) was obtained.
Preparation of Standard Solution
Entecavir anhydride 20 mg was put into a 20 ml flask with mobile phase. The mixed solution was sonicated and stirred. As a result, a standard solution (0.1 mg/ml) was obtained.
HPLC Condition
Detector: UV (254 nm)
Column: ODS, 250×4.6 mm, 5 μm
Flow rate: 1.0 ml/min
Mobile Phase
A: ACN:DW–3:97
B: ACN
<Gradient Condition>

| Time | A | B |
|---|---|---|
| 0.0 | 100 | 0 |
| 8.0 | 100 | 0 |
| 50.0 | 77 | 23 |

-continued

| Time | A | B |
|---|---|---|
| 75.0 | 17 | 83 |
| 75.1 | 100 | 0 |
| 90.0 | 100 | 0 |

Assay (%)

Assay (%)=$At/As \times Cs/Ct \times P$

At: Area response of entecavir in test sample solution
As: Area response of entecavir in standard sample solution
Ct: entecavir concentration of test sample solution
Cs: entecavir concentration of standard sample solution
P: Purity of desmopressin acetate standard (%)
Total Impurities (%)

Total Impurities=Total of Individual Impurities

Individual Impurity (%)=$Ai/At \times 100$

Ai: Area response of impurity in test sample solution
At: Area response of entecavir in test sample solution
LOD (Loss on Drying)

According to the method described in USP 731, LOD test was conducted at 105° C. for 4 hours.

Disintegration Time

Tested by using a calibrated stopwatch according to USP 701.

Test Example 1. Stabilizing Effect of Antioxidizing Agent

An orally dissolving film was prepared by the preparation method mentioned in Example 1 with the ingredients and amounts thereof described in the following Table 1.

For LOD (%), the orally dissolving film is dried and then moisture content contained in the orally dissolving film can be figured out based on weight difference value of the orally dissolving film before and after drying. For example, in the following Table 1, LOD (%) of Example 1 was 7.8%, and it was understood that 7.8% of moisture contained in the orally dissolving film was lost. When LOD (%) was less than 10.0%, it is considered to be suitable for an orally dissolving film.

Disintegration time refers to time spent for disintegrating (dissolving) an orally dissolving film, and when it is less than 1 min, it is considered to be suitable for an orally dissolving film.

TABLE 1

| Ingedients | Ref. | Examples (%) | | | | | | | |
|---|---|---|---|---|---|---|---|---|---|
| | | 1 | 2 | 3 | 4 | 5 | 6 | 7 | 8 |
| API | | | | | 1.210 | | | | |
| Butylated hydroxytoluene | — | 0.001 | — | 0.012 | — | 0.024 | — | 0.040 | — |
| Butylated hydroxyanisole | — | — | 0.001 | — | 0.012 | — | 0.024 | — | 0.040 |
| Polymer | 84.890 | 84.889 | 84.889 | 84.878 | 84.878 | 84.866 | 84.866 | 84.850 | 84.850 |
| Plasticizer | | | | | 8.000 | | | | |
| Diluent | | | | | 5.000 | | | | |
| Surfactant | | | | | 0.100 | | | | |
| Sweetning agent | | | | | 0.300 | | | | |
| Pigment | | | | | Q.S | | | | |
| Flavor | | | | | Q.S | | | | |
| Water | | | | | Q.S | | | | |
| Total (as solid) | | | | | 100.000% | | | | |
| LOD (%) | 7.5 | 7.8 | 7.1 | 8.0 | 7.3 | 7.2 | 7.9 | 7.3 | 7.3 |
| Disintegration time (min.) | <0.5 | <0.5 | <0.5 | <1.0 | <1.0 | <1.0 | <1.0 | <1.0 | <1.0 |

| Ingedients | Examples (%) | | | | | |
|---|---|---|---|---|---|---|
| | 9 | 10 | 11 | 12 | 13 | 14 |
| API | | | 0.605 | | | |
| Butylated hydroxytoluene | 60.500 | — | 18.150 | — | 6.050 | — |
| Butylated hydroxyanisole | — | 60.500 | — | 18.150 | — | 6.050 |
| Polymer | 24.995 | 24.995 | 67.345 | 67.345 | 79.445 | 79.445 |
| Plasticizer | | | 8.000 | | | |
| Diluent | | | 5.000 | | | |
| Surfactant | | | 0.100 | | | |
| Sweetning agent | | | 0.300 | | | |
| Pigment | | | Q.S | | | |
| Flavor | | | Q.S | | | |
| Water | | | Q.S | | | |
| Total (as solid) | | | 100.000% | | | |
| LOD (%) | 7.6 | 7.7 | 7.4 | 7.8 | 7.2 | 7.0 |
| Disintegration time (min.) | >20.0 | >20.0 | <10.0 | <10.0 | <1.0 | <1.0 |

All of Comparative Example and Examples 1 to 14 showed LOD (%) of 7.0% or more due to characteristics of the orally disintegrating (dissolving) formulation. Namely, it was confirmed that whether an antioxidizing agent is added or not, or the amount of an antioxidizing agent added dose not affect LOD (%).

On the other hand, disintegrating time of Examples 1 to 8 and 13 to 14 was less than 1 min, but disintegrating time of Examples 9 to 12 was more than 1 min, thereby confirming that it takes long time to dissolve the orally disintegrating films. Namely, it was found that dissolving time of an orally disintegrating film may vary depending on weight ratio of entecavir:antioxidizing agent.

Stability test was conducted under harsh condition (40±2° C., relative humidity 60±5%), and in order to block contact between external moisture and a preparation, a pharmaceutical preparation was put in a multi-layered aluminum foil container and sealed for conducting the test.

Assay (%) relates to the amount of entecavir maintained in a pharmaceutical preparation, and change amount (%) is an assay (%) change value over time. Through the value, whether the amount of entecavir in a pharmaceutical preparation is changed or not over time can be found. In this test, assay (%) was measured at week 0, week 4 and week 8, and difference between assay (%) at week 0 and assay (%) at week 8 was recorded as change amount (%).

Total impurities (%) relates to the amount of impurities from entecavir measured in a pharmaceutical preparation, and change amount (%) is a total impurities (%) change value over time. Through the value, change of entecavir impurity generation amount in a pharmaceutical preparation over time can be found. In this test, total impurities (%) was measured at week 0, week 4 and week 8, and difference between total impurities (%) at week 0 and total impurities (%) at week 8 was recorded as change amount (%).

In the case using an antioxidizing agent, it can be found that there was very little change on change amount (%) because total impurities (%) of less than 0.1% was maintained during storage period under harsh condition. Namely, it can be found that there was almost no impurity generation during storage period.

Further, assay (%) of 97.0 to 103.0% was maintained during storage period under harsh condition, and therefore, it can be found that there was very little change on change amount (%). Namely, it can be found that entecavir was maintained during storage period without being hydrolyzed by moisture.

As can be seen from the results of Table 1 and Table 2, in the case using an antioxidizing agent, it can be found that entecavir is maintained without being hydrolyzed despite the moisture contained in a preparation. Just, it can be found that when weight ratio of entecavir:antioxidizing agent was increased, disintegrating time was increased, thereby having a disadvantage as an orally disintegrating formulation.

Test Example 2. Stabilizing Effect by Antioxidizing Agent Type

An orally dissolving film was prepared by the preparation method mentioned in Example 1 with the ingredients and amounts thereof described in the following Table 3.

For LOD (%), the orally dissolving film is dried and then moisture content contained in the orally dissolving film can be figured out based on weight difference value of the orally dissolving film before and after drying. When LOD (%) was less than 10.0%, it is considered to be suitable for an orally dissolving film.

TABLE 2

| Contents | period (weeks) | Ref | Examples 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| Assay (%) | 0 | 101 | 101 | 99.4 | 102 | 101 | 99.1 | 100 | 101 | 101 | 102 | 99.7 | 100 | 102 | 101 | 101 |
|  | 4 | 96.1 | 101 | 98.6 | 101 | 101 | 98.5 | 99.8 | 101 | 100 | 102 | 99.9 | 100 | 102 | 101 | 100 |
|  | 8 | 91.9 | 100 | 97.9 | 101 | 100 | 98.8 | 99.6 | 101 | 101 | 102 | 99.7 | 100 | 102 | 101 | 100 |
| Change amount (%) |  | −9.0 | −0.7 | −1.5 | −0.3 | −1.1 | −0.3 | −0.7 | 0.2 | −0.3 | 0.1 | 0.0 | −0.1 | −0.3 | −0.1 | −0.3 |
| Judgement |  | poor | bad | poor | very good | poor | very good | bad | very good | very good | very good | very good | very good | very good | very good | very good |
| Total impurity (%) | 0 |  |  |  |  |  |  |  | ≤0.1 |  |  |  |  |  |  |  |
|  | 4 | ≤1.1 | ≤0.2 | ≤0.4 | ≤0.2 | ≤0.2 | ≤0.2 | ≤0.2 | ≤0.1 | ≤0.1 | ≤0.1 | ≤0.1 | ≤0.1 | ≤0.1 | ≤0.1 | ≤0.1 |
|  | 8 | ≤1.9 | ≤0.5 | ≤0.7 | ≤0.4 | ≤0.4 | ≤0.2 | ≤0.2 | ≤0.1 | ≤0.1 | ≤0.1 | ≤0.1 | ≤0.1 | ≤0.1 | ≤0.1 | ≤0.1 |
| Change amount (%) |  | 1.8 | 0.4 | 0.6 | 0.3 | 0.3 | 0.1 | 0.1 | 0 | 0 | 0 | 0 | 0 | 0 | 0 | 0 |
| Judgement |  | poor | bad | bad | good | good | very good | very good | very good | very good | very good | very good | very good | very good | very good | very good |

|  | Change amount |
|---|---|
| Assay Judgement |  |
| Very good | ≤±0.3% |
| Good | −0.3%~−0.5% |
| Bad | −0.5%~−1.0% |
| Poor | ≥−1.0% |
| Impurity Judgement |  |
| Very good | ≤0.1% |
| Good | 0.1%~0.3% |
| Bad | 0.3%~1.0% |
| Poor | ≥1.0% |

TABLE 3

| Indredients | Ref | [API:Antioxidizing agent - 1:1] | | | | | | | | [API: Antioxidizing agent - 1:80] (%) | | | | | |
|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 |
| API | | | | | 1.210 | | | | 50.000 | | | 0.625 | | | | |
| Butylated hydroxytoluene | — | 1.210 | — | — | — | — | — | — | 50.000 | — | — | — | — | — | — |
| Butylated hyroxyanisole | — | — | 1.210 | — | — | — | — | — | — | 50.000 | — | — | — | — | — |
| Tocopherol | — | — | — | 1.210 | — | — | — | — | — | — | 50.000 | — | — | — | — |
| Citric acid anhydrous | — | — | — | — | 1.210 | — | — | — | — | — | — | 50.000 | — | — | — |
| Ascorbic acid | — | — | — | — | — | 1.210 | — | — | — | — | — | — | 50.000 | — | — |
| EDTA | — | — | — | — | — | — | 1.210 | — | — | — | — | — | — | 50.000 | — |
| D-mannitol | — | — | — | — | — | — | — | 1.210 | — | — | — | — | — | — | 50.000 |
| Polymer | | | 83.680 | | | | | | | | | 35.475 | | | | |
| Plasticizer | | | | | | | | | 8.000 | | | | | | | |
| Diluent | | | | | | | | | 5.000 | | | | | | | |
| Surfactant | | | | | | | | | 0.100 | | | | | | | |
| Sweetning agent | | | | | | | | | 0.300 | | | | | | | |
| Pigment | | | | | | | | | Q.S | | | | | | | |
| Flavor | | | | | | | | | Q.S | | | | | | | |
| Water | | | | | | | | | Q.S | | | | | | | |
| Total (as solid) | | | | | | | | | 100.000% | | | | | | | |
| LOD (%) | 7.5 | 7.8 | 7.6 | 7.6 | 7.8 | 7.5 | 7.5 | 7.4 | 8.0 | 8.5 | 8.2 | 7.9 | 8.1 | 8.3 | 8.1 |

Comparative Example and all of Examples 1 to 14 showed less than 10.0% of LOD (%). Just, all showed 7.0% or more of LOD (%) due to characteristics of the orally disintegrating (dissolving) formulation. Namely, it was confirmed that whether an antioxidizing agent is added or not, or the antioxidizing agent type dose not affect LOD (%). Further, according to the results of stability test in the following Table 4, it was confirmed that LOD (%) also does not affect moisture stability of entecavir.

Stability test was conducted under harsh condition (40±2° C., relative humidity 60±5%), and in order to block contact between external moisture and a preparation, a pharmaceutical preparation was put in a multi-layered aluminum foil container and sealed for conducting the test.

Assay (%) relates to the amount of entecavir maintained in a pharmaceutical preparation, and change amount (%) is an assay (%) change value over time. Through the value, whether the amount of entecavir maintained in a pharmaceutical preparation is changed or not over time can be found. In this test, assay (%) was measured at week 0, week 4 and week 8, and difference between assay (%) at week 0 and assay (%) at week 8 was recorded as change amount (%).

Total impurities (%) relates to the amount of impurities from entecavir measured in a pharmaceutical preparation, and change amount (%) is a total impurities (%) change value over time. Through the value, change of entecavir impurity generation amount in a pharmaceutical preparation over time can be found. In this test, total impurities (%) was measured at week 0, week 4 and week 8, and difference between total impurities (%) at week 0 and total impurities (%) at week 8 was recorded as change amount (%).

TABLE 4

| Contents | period (weeks) | Examples | | | | | | | | | | | | | | |
|---|---|---|---|---|---|---|---|---|---|---|---|---|---|---|---|---|
| | | Ref | 1 | 2 | 3 | 4 | 5 | 6 | 7 | 8 | 9 | 10 | 11 | 12 | 13 | 14 |
| Assay (%) | 0 | 102 | 100 | 101 | 101 | 99.2 | 99.8 | 99.3 | 103 | 100 | 99.5 | 102 | 102 | 101 | 102 | 102 |
| | 4 | 97.3 | 99.9 | 101 | 99.1 | 96.1 | 95.6 | 96.1 | 98.1 | 101 | 99.5 | 102 | 101 | 100 | 101 | 97.5 |
| | 8 | 93.2 | 100 | 102 | 97.9 | 93 | 92.7 | 94.4 | 94.6 | 100 | 99.3 | 101 | 100 | 98.8 | 100 | 94.2 |
| Change amount (%) | | −8.3 | 0.2 | 0.2 | −3.1 | −6.2 | −7.1 | −4.9 | −8.0 | −0.1 | −0.2 | −0.5 | −2.0 | −2.3 | −1.3 | −7.4 |
| Judgement | | poor | very good | very good | poor | poor | poor | poor | poor | very good | very good | good | poor | poor | poor | poor |
| Total impurity (%) | 0 | | | | | | | ≤0.1 | | | | | | | | |
| | 4 | ≤1.0 | ≤0.1 | ≤0.1 | ≤0.5 | ≤0.8 | ≤0.9 | ≤0.6 | ≤1.0 | ≤0.1 | ≤0.1 | ≤0.2 | ≤0.3 | ≤0.3 | ≤0.2 | ≤0.7 |
| | 8 | ≤1.7 | ≤0.1 | ≤0.1 | ≤0.9 | ≤1.1 | ≤1.5 | ≤0.9 | ≤1.6 | ≤0.1 | ≤0.1 | ≤0.2 | ≤0.4 | ≤0.4 | ≤0.4 | ≤1.2 |
| Change amount (%) | | 1.6 | 0 | 0 | 0.8 | 1.0 | 1.4 | 0.8 | 1.5 | 0 | 0 | 0.1 | 0.3 | 0.3 | 0.3 | 1.1 |
| Judgement | | poor | very good | very good | bad | bad | poor | bad | poor | very good | very good | very good | good | good | good | poor |

| | Change amount |
|---|---|
| Assay Judgement | |
| Very good | ≤±0.2% |
| Good | −0.2%~−0.5% |
| Bad | −0.5%~−1.0% |
| Poor | ≥−1.0% |
| Impurity Judgement | |
| Very good | ≤0.1% |
| Good | 0.1%~0.3% |

TABLE 4-continued

| | |
|---|---|
| Bad | 0.3%~1.0% |
| Poor | ≥1.0% |

In the case using the excessive amount of the antioxidizing agent, i.e., weight ratio of entecavir:antioxidizing agent is 1:80, all showed excellent water-stability regardless of antioxidizing agent type, but in the case using the very small amount of the antioxidizing agent, i.e., weight ratio of entecavir:antioxidizing agent is 1:1, only the case using butyl hydroxy toluene, butyl hydroxy anisole as an antioxidizing agent showed moisture-stability.

Example 2. Preparation of Orally Disintegrating Tablet Comprising Entecavir as Active Ingredient Entecavir and an antioxidizing agent were dissolved in a proper solvent, and then mixed with an excipient to prepare granule. The granule was dried and sized to a certain size. An excipient, a binding agent, a disintegrating agent, a lubricant, a sweetening agent and the like were added thereto, and tableted by a single tablet press to prepare an orally disintegrating tablet comprising entecavir. Moisture content based on dry weight of the orally disintegrating tablet was LOD (%) of 1% or more but less than 7%, measured at 105° C. for 4 hours in accordance with USP 731.

Example 3. Preparation of Granule/Powder Comprising Entecavir as Active Ingredient Entecavir, an antioxidizing agent and a binding agent were dissolved in a proper solvent, and then sprayed to a mixture of an excipient and a disintegrating agent in a fluid bed granulator to prepare a granule. The granule was mixed with an excipient, a sweetening agent and a flavor to prepared granule/powder comprising entecavir. Moisture content based on dry weight of the granule/powder was LOD (%) of 1% or more but less than 7%, measured at 105° C. for 4 hours in accordance with USP 731.

INDUSTRIAL APPLICABILITY

According to the present invention, the invention has an effect that entecavir can be stably maintained in a pharmaceutical preparation containing a certain amount or more of moisture by adding the antioxidizing agent, thereby a pharmaceutical preparation can be provided as a formulation containing a certain amount or more of moisture, for example, an orally disintegrating film formulation.

The present disclosure has been described in detail. However, it should be understood that the detailed description and specific examples, while indicating preferred embodiments of the disclosure, are given by way of illustration only, since various changes and modifications within the scope of the disclosure will become apparent to those skilled in the art from this detailed description.

What is claimed is:

1. A pharmaceutical preparation comprising entecavir and at least one antioxidizing agent, and having an LOD (%) of 1% or more but less than 10%, which is measured at 105° C. for 4 hours in accordance with USP 731,
    wherein the antioxidizing agent is butyl hydroxyl toluene, butyl hydroxyl anisole, or a mixture thereof, and
    wherein the weight ratio of entecavir and the antioxidizing agent is 100:1 to 1:30.

2. The pharmaceutical preparation of claim 1, wherein weight ratio of entecavir and the antioxidizing agent is 30:1 to 1:10.

3. The pharmaceutical preparation of claim 1, wherein the pharmaceutical preparation is a pharmaceutical preparation for treating or preventing hepatitis.

4. The pharmaceutical preparation of claim 1, wherein the pharmaceutical preparation is an orally disintegrating film formulation.

5. The pharmaceutical preparation of claim 4, wherein moisture content of the orally disintegrating film formulation is LOD (%) of 2% or more but less than 10%, which is measured at 105° C. for 4 hours in accordance with USP 731.

6. A method for preparing the pharmaceutical preparation of claim 1, the method comprising:
    adding at least one antioxidizing agent and entecavir; and
    drying the pharmaceutical preparation to have moisture content of 1% or more but less than 10% of LOD (%), which is measured at 105° C. for 4 hours in accordance with USP 731,
    wherein the antioxidizing agent is butyl hydroxyl toluene, butyl hydroxyl anisole, or a mixture thereof, and
    wherein the weight ratio of entecavir and the antioxidizing agent is 100:1 to 1:30.

* * * * *